(12) United States Patent
Lindner et al.

(10) Patent No.: US 10,893,889 B2
(45) Date of Patent: Jan. 19, 2021

(54) PEDICLE SCREW SYSTEM COMPRISING A LOCKING SCREW WITH THREADED CHAMFER

(71) Applicant: Aesculap AG, Tuttlingen (DE)

(72) Inventors: Stephan Lindner, Wurmlingen (DE); Sven Krüger, Trossingen (DE); Alexander Haas, Donaueschingen (DE)

(73) Assignee: AESCULAP AG, Tuttlingen (DE)

( * ) Notice: Subject to any disclaimer, the term of this patent is extended or adjusted under 35 U.S.C. 154(b) by 26 days.

(21) Appl. No.: 16/319,098

(22) PCT Filed: Jul. 20, 2017

(86) PCT No.: PCT/EP2017/068332
§ 371 (c)(1),
(2) Date: Jan. 18, 2019

(87) PCT Pub. No.: WO2018/015482
PCT Pub. Date: Jan. 25, 2018

(65) Prior Publication Data
US 2020/0197049 A1   Jun. 25, 2020

(30) Foreign Application Priority Data
Jul. 21, 2016   (DE) .......................... 10 2016 113 495

(51) Int. Cl.
*A61B 17/70* (2006.01)
(52) U.S. Cl.
CPC ................... *A61B 17/7032* (2013.01)
(58) Field of Classification Search
CPC .................. A61B 17/7032; A61B 17/7035; F16B 35/047

USPC ......... 606/270, 273, 275, 316; 411/386, 393
See application file for complete search history.

(56) References Cited

U.S. PATENT DOCUMENTS

| 7,780,706 B2 | 8/2010 | Marino et al. |
| 8,257,402 B2 | 9/2012 | Jackson |
| 2004/0167526 A1* | 8/2004 | Jackson ............... F16B 35/047 606/278 |

(Continued)

FOREIGN PATENT DOCUMENTS

| DE | 202005007495 U1 | 8/2005 |
| DE | 102014108225 A1 | 12/2015 |

(Continued)

OTHER PUBLICATIONS

German Search Report for German Application No. 10 2016 113 495.3, dated Feb. 20, 2017, with English translation—15 pages.

(Continued)

*Primary Examiner* — Eduardo C Robert
*Assistant Examiner* — David C Comstock

(57) ABSTRACT

A bone screw system includes a bone screw having a tulip that forms a seat for a longitudinal support for surgical connection of adjacent bone screws. The tulip has a tulip thread into which a clamping screw is screwed. The clamping screw has a clamping screw thread for locking the longitudinal support by clamping within the seat. The clamping screw thread is provided on the run-in side with a thread chamfer. The thread chamfer is introduced to the clamping screw thread while chamfering a thread elevation in the radial direction.

20 Claims, 4 Drawing Sheets

(56) References Cited

U.S. PATENT DOCUMENTS

| | | | |
|---|---|---|---|
| 2005/0187549 A1* | 8/2005 | Jackson | A61B 17/7032 606/60 |
| 2005/0216000 A1* | 9/2005 | Colleran | A61B 17/7037 606/60 |
| 2008/0234759 A1 | 9/2008 | Marino | |
| 2011/0318136 A1 | 12/2011 | Toyonaga et al. | |
| 2013/0197585 A1* | 8/2013 | Jackson | A61B 17/8685 606/278 |
| 2014/0018867 A1 | 1/2014 | Freudiger et al. | |
| 2014/0142633 A1* | 5/2014 | Jackson | A61B 17/7002 606/273 |
| 2014/0350605 A1 | 11/2014 | Kirschman | |

FOREIGN PATENT DOCUMENTS

| | | |
|---|---|---|
| EP | 2674123 A1 | 12/2013 |
| WO | 2010038446 A1 | 4/2010 |
| WO | 2012103660 A1 | 8/2012 |

OTHER PUBLICATIONS

International Search Report and Written Opinion for Application No. PCT/EP2017/068332, dated Oct. 25, 2017—9 pages.

\* cited by examiner

PEDICLE SCREW SYSTEM COMPRISING A LOCKING SCREW WITH THREADED CHAMFER

RELATED APPLICATIONS

This application is the United States national phase entry of International Application No. PCT/EP2017/068332, filed Jul. 20, 2017, which claims the benefit of priority of German Application No. 10 2016 113 495.3, filed Jul. 21, 2016. The contents of International Application No. PCT/EP2017/068332 and German Application No. 10 2016 113 495.3 are incorporated by reference herein in their entireties.

FIELD

The present invention relates to a bone screw system, especially a pedicle screw system, which includes a bone screw, especially a pedicle screw, comprising a receiving sleeve or tulip provided especially at the screw head which forms a seat for a longitudinal support for surgical connection of adjacent bone screws and, resp., pedicle screws and is provided with a tulip thread, and a clamping screw adapted to be screwed into the tulip thread of the receiving sleeve comprising a clamping screw thread for locking the longitudinal support by clamping in the seat, wherein the clamping screw thread is provided with a thread cut/a thread chamfer. Furthermore, the invention relates to a corresponding clamping screw for the bone screw system.

BACKGROUND

Bone and pedicle screws are known from the state of the art. They serve for dorsal stabilization of the vertebral column by means of transpedicular screwing. Accordingly, pedicle screws are placed in the pedicles of respective adjacent vertebrae whereupon an angularly stable connection is made between the axially superimposed pedicle screws and an axially extending longitudinal support or land which is locked by means of a clamping screw with respect to the bone or pedicle screw. The pedicle screws and longitudinal supports constitute a vertebral stabilizing system.

Usually a pedicle screw includes a screw shank extending in the axial direction and having a male thread to which a receiving sleeve, the so-called tulip, is connected on the screw head side. Said tulip is substantially U-shaped having opposite wall portions (sleeve flanks) and a gap formed therebetween and extending in the radial direction as a seat for the longitudinal support or land. The tulip is provided with a tulip thread extending in the axial direction. The longitudinal support is inserted in the gap of the tulip in the radial direction and is fixed by means of the clamping screw which is also referred to as locking screw or set screw and is screwed with the tulip thread.

In pedicle screw systems, the problem is known that it is not always easy to insert the clamping screw into the tulip head. The reason for this resides, inter alia, in little thread backlash between the tulip thread of the pedicle screw and the clamping screw thread of the clamping screw. By providing more thread backlash the problem cannot be solved in a satisfactory manner as the thread backlash has to be little due to the small encompassing of the two thread parts as well as a safe clamping effect and, otherwise, the functional safety and the clamping would be impaired.

The problem is usually moreover aggravated by the fact that with manipulation by instruments forces are exerted on the implant. They may result in the tulip head elastically deforming, especially deforming inwardly. For example, when attaching the clamping screw to a pedicle screw for fixing the longitudinal support, the tulip may be deformed by forces acting on the pedicle screw and especially on the tulip thereof, for example when vertebral bodies are manipulated or the longitudinal support is pressed. In this way, the geometry of the tulip thread varies, for example the inner diameter thereof decreases, thus additionally impeding or preventing screwing of the clamping screw.

Basically, two types of deformations may occur, namely those in which the tulip thread is deformed in the direction of the clamping screw thread and those of the opposite direction. In the case of the first-mentioned deformations, such deformations which prevent the set screw from being attached to the tulip thread are especially difficult, because the threads are no longer adapted to mesh. However, even in the case of a minor deformation which still permits screwing, due to the deformation of the tulip an inclination of the set screw relative to the axis of the tulip may occur. This may result in the fact that the thread cut/thread chamfer, especially that of the set screw, is damaged. A so-called "cross-threading" may occur, meaning that the set screw is inclined toward the longitudinal axis of the screw shank and the male thread thereof so far that to the start of the thread of the set screw, viz. the run-in pitch or run-in pitches, engages or engage in the wrong pitch of the female thread of the tulip, which may entail damage of the thread to uselessness of the set screw and/or the pedicle screw.

From US 2014/0350605 A1 a pedicle screw system is known in which a clamping screw includes a cut/chamfered head area facilitating attachment in a female thread formed within the tulip. In addition, the female thread of the tulip includes a shortened first thread pitch so that the clamping screw can be inserted and centered by means of the chamfered head area initially without thread engagement in the tulip and, after that, is turned at this position with a thread engagement being brought about. The shortening of the thread pitch under certain circumstances may disadvantageously constitute a weakening of the thread.

From U.S. Pat. No. 7,780,706 B2 a similar pedicle screw system is known in which a clamping screw is provided with a step in the area of its thread run-in. The step has a diameter smaller than the inner thread diameter of the clamping screw thread. Toward the clamping screw thread the step ends by a shoulder which extends transversely to the longitudinal axis/screw axis of the clamping screw. Due to this alignment of the shoulder, the thread is chamfered orthogonally to the longitudinal axis of the clamping screw. In this way, the first thread pitch is chamfered on the run-in side such that the radially outwardly extending thread profile (the thread elevation delimited by thread flanks) continuously increases in thickness in wedge shape in the circumferential direction starting with a crest, until the shoulder does no longer intersect any one of the thread flanks of the first thread pitch (FIG. 1 illustrates such known clamping screw in a lateral view). It can also be said that in this clamping screw the thread chamfer is introduced in the radial direction to the clamping screw at constant depth and, when viewed in the circumferential direction, advances in the axial direction into the thread pitch. With such chamfer of the thread it is a particular drawback that the chamfered thread elevation in portions, especially close to the crest, is very thin and is thus very sensitive. For example, it may easily deform when being screwed in.

From U.S. Pat. No. 8,257,402 B2 a closure for a surgical implant receiving a rod in the form of a clamping screw with a male thread is known in which a chamfer is formed on the run-in side of the male thread. By the chamfer the clamping screw is provided on its end face with a circumferential beveling which facilitates insertion into a female thread of the implant. In this case, too, the first thread pitch is chamfered on the run-in side such that the thread profile extending radially outwardly (the thread elevation delimited by thread flanks) in the circumferential direction continuously increases in thickness in wedge shape starting with a crest, until the chamfer does no longer intersect any one of the thread flanks of the first thread pitch (FIG. 2 illustrates such known clamping screw in a lateral view). In this case, too, it can be stated that the thread chamfer is introduced or formed with a constant radial depth. It is equally a drawback that the chamfered thread elevation in portions, especially close to the crest, is very thin and thus sensitive. It may easily deform when being screwed in, for example.

SUMMARY

Since deformations of the pedicle screw and especially of the tulip cannot always be safely avoided, based on the afore-described state of the art the object underlying the invention is to provide a bone screw system, especially a pedicle screw system, which is robust with respect to such deformations and facilitates attachment of a clamping screw to a bone or pedicle screw and renders the same safer without any additional elements or instruments such as guide sleeves etc. being required for this purpose or the operating surgeon's view being obstructed. The clamping screw is intended to be adapted to be easily screwed in, even if the tulip head is deformed elastically inwardly by forces acting from outside. Moreover, the system is intended to be robust and stable, especially the risk of damage of the clamping screw thread, in particular of the thread run-in thereof, is to be reduced during screwing.

This object is achieved by a clamping screw and, resp., by a bone screw or pedicle screw system as described herein. In accordance with the invention, the clamping screw thread on the run-in side has a thread cut/chamfer at which the clamping screw thread is reduced or, especially completely, withdrawn in the radial direction.

The present description is made with reference to a bone screw. However, the invention especially relates to a pedicle screw. The term "bone screw" therefore has to be understood as being focused on a pedicle screw and vice versa.

Other than in the afore-described state of the art, the thread cut/thread chamfer is not configured in such way that the first thread pitch is chamfered in the axial direction but in such way that the first thread pitch is chamfered in the radial direction. It can also be stated that the thread and, resp., the thread elevation is flattened or withdrawn by the (radial) thread chamfer, especially flattened or withdrawn in the radial direction toward the central longitudinal axis of the clamping screw. On the other hand, the thread chamfer according to the invention is configured to run out in the axial direction, whereas in the afore-described state of the art it is constant in its circumferential extension in the axial direction. According to the invention, the smallest extension of the thread chamfer in the axial direction preferably is no less than 0.5 mm.

The invention allows to achieve the advantage that the thread crest and, resp., the distance between the thread flanks in the area of the thread chamfer is not tapered and thus weakened. Rather, the thread cross-section in the axial direction is completely maintained also in the area of the thread chamfer. Hence the part of the clamping screw thread first engaging in the tulip thread when the clamping screw is screwed into the tulip of the bone screw is especially stable and robust so that deformations thereof can be prevented or at least substantially reduced. Nevertheless, in the bone screw system according to the invention screwing of the clamping screw into the tulip thread is especially facilitated due to the thread chamfer.

According to the invention, on the run-in side of the tulip thread a guide is provided for a clamping screw to be screwed into the thread without the thread being weakened by the guide. Said guide is configured so that, even if the tulip is deformed, the clamping screw can be easily positioned at the thread run-in thereof and can be screwed into the same. In this way, despite deformation mutual engagement of the tulip thread and the clamping screw thread is ensured. In other words, by the thread chamfer a portion with a defined radial backlash and without any mutual thread engagement is provided between the clamping screw and the tulip so that deformations of the tulip can be compensated. The clamping screw in this way can be easily and safely arranged on the tulip even if the latter is deformed and can be positioned relative to the tulip thread. It is a particular advantage that the clamping screw is to be correctly positioned on the pedicle screw by an operating surgeon, even if his/her view is obstructed, and is guided and supported before the threads are in mutual engagement. Therefore, no special efforts or additional instruments are required to bring the clamping screw into the position defined for screwing into the tulip with the required accuracy when attaching the clamping screw to the tulip thread. The operating surgeon can also haptically detect the seat of the clamping screw delimited or defined by the thread chamfer so that intended screwing is facilitated and misfits of the clamping screw relative to the pedicle screw are safely avoided. An operating surgeon is no longer required to pay special attention to the attachment of the set screw, which entails considerable ease of operation and time benefits. When the clamping screw guided by the thread chamfer now rotates about its own thread axis, the threads of the clamping screw and of the tulip are engaged. The clamping screw is advanced also in the axial direction due to its screwing motion. Due to the axial displacement of the clamping screw in the direction of the pedicle screw, deformation of the latter, especially of the sleeve flanks, may be reset. As a result, by the invention a clamping screw can be easily attached to a pedicle screw which is being loaded and therefore deformed and can be screwed therewith.

One embodiment of the invention is characterized in that the thread chamfer has a circumferential surface. Said circumferential surface may be formed especially in parallel to the central longitudinal axis of the clamping screw. The circumferential surface according to the invention may act or be configured as a type of guide surface by means of which the clamping screw can be positioned and guided relative to the tulip before an actual mutual thread engagement with the tulip thread and can be especially inserted in the seat even if the tulip is deformed.

In one embodiment of the invention, the thread chamfer may have a transition section (between the chamfered thread and the non-chamfered thread) which acts as a run-in portion or a run-out portion depending on the viewing direction. In this transition section, the circumferential surface may have a varying radial distance from the central longitudinal axis of the clamping screw. Accordingly, it forms a type of transition from the thread chamfer to the clamping screw thread and is arranged especially on the side of the thread chamfer directed toward the clamping screw thread.

The radial distance of the circumferential surface from the central longitudinal axis preferably corresponds to the outer thread radius on the run-out side of the transition section. In this way, a smooth transition from the thread chamfer to the clamping screw thread is formed, thus enabling the clamping screw to be screwed in without getting stuck or jammed. The radial distance of the circumferential surface from the central longitudinal axis on the run-in side of the transition section (i.e. in a particular angular range) may be especially smaller than or equal to the thread core radius. In other words, the thread core is flattened in the circumferential direction ahead of the chamfer of the male thread (transitional chamfer), preferably over a range of a maximum of 90-180° or less. In this manner, the clamping screw is provided with a guide portion formed by the thread chamfer the diameter of which is smaller than the core diameter of the tulip thread so that even if the tulip is deformed, it is possible to easily attach the clamping screw and engage the two threads with each other.

One embodiment of the invention is characterized in that the radial distance of the circumferential surface of the transition section from the central longitudinal axis varies continuously and/or constantly in the circumferential extension. This promotes gradual re-forming of the tulip in the case of deformation of the same. The variation may be especially linear or curved or circular arc-shaped.

In a preferred embodiment, the clamping screw may form, due to the variation of the radial distance of the circumferential surface from the longitudinal axis, a non-circular (cross-sectional) profile at the front end. Due to said non-circular profile, the clamping screw has an inserting position with an inserting function and a splaying position with a splaying function. In particular, the radial distance of the circumferential surface on the run-out side of the transition section corresponds to the outer thread radius (nominal radius of the thread) and is larger than the radial distance of the circumferential surface from the central longitudinal axis on the run-in side of the transition section. This is resulting, at the front end of the clamping screw, in different distances of points on the circumferential surface diametrically opposed in the radial direction and, resp., of one point on the circumferential surface from one point on the surface of the outer thread radius of the first thread elevation. Each of the connecting lines of the points intersects the central longitudinal axis. The distance of two diametrically opposed points will hereinafter be referred to as diameter. Hence, the clamping screw has at least two different diameters at the front end. Preferably, a maximum diameter is orthogonal to a minimum diameter. When interacting with the tulip of the pedicle screw, the clamping screw shows two different positions having two different functions. In a first position or inserting position having an inserting function, the circumferential surfaces are adjacent to the flanks of the (deformed) tulip and, resp., the tulip arms outside the transition area. The clamping screw can be inserted into the tulip via the accompanying smaller diameter (smaller than the maximum diameter). Subsequently, the clamping screw is screwed into the tulip, by means of rotation, in the second position or, resp., splaying position having a splaying function. The transition area with the increasing radial distance of the circumferential surface is screwed between the two flanks of the tulip by the movement of rotation. The increase in the diameter between the flanks of the tulip is splaying the flanks of the tulip. Thus, in the second position the transition area, especially the transition area on the run-out side, or the radial outer surface of the first thread elevation is adjacent to the flank of the tulip. The splayed position is preferably rotated by 90 degrees with respect to the inserting position. This helps to facilitate screwing of a clamping screw with small tolerances and, resp., with very small thread backlash without reducing a maximum diameter ("splaying diameter").

The transition section may extend especially in the circumferential direction over an angular section a between approx. 20° and approx. 80°, preferably between approx. 40° and approx. 135°, more preferred between approx. 60° and approx. 90°. In this way, a sufficiently large guiding area is formed which enables the clamping screw to be attached even in the case of relatively large deformations of the clamping screw.

According to one embodiment of the invention, in a subarea the thread chamfer is formed in pitch cylinder shape having a constant radial distance from the central longitudinal axis. In this subarea, the radial distance from the central longitudinal axis may be especially smaller than the thread core radius. The subarea having a constant radial distance may extend in the circumferential direction especially over an angular area β of at least 90°, preferably of from 90° to 180°.

One embodiment of the invention is characterized in that the thread chamfer ends where the first complete thread elevation of the thread pitch starts and, resp., where the thread crest has its full/normal width. In this manner, the first area of the clamping screw thread forming a thread engagement with the tulip thread is configured so that it is very robust and is not inadvertently deformable.

It is of particular advantage when the thread chamfer is designed to follow the lead of the clamping screw thread. In such case it can be said that the thread chamfer is formed to have the same lead as the clamping screw thread. In this way, the clamping screw thread is chamfered and weakened nowhere in the axial direction so that it is especially robust.

Summing up, it can be stated that the invention provides a thread chamfer which may have its starting point at the location of the thread run-out, hence at the point from which the flank width of the thread is reduced. The thread chamfer may start at the point from which the flank width would be diminished by the thread run-out, unless there would be a chamfer. The thread chamfer can be reduced by means of the transition area to a core diameter smaller than the thread core diameter. Said (reduced) core diameter may extend over a portion of at least 90°. Said core diameter need not be round, rather all portions, related to the diameter, are intended to be smaller than the thread core diameter.

The invention especially provides the following advantages:
robust thread chamfer
simple screwing in of the locking screw
no weakening of the thread.

BRIEF DESCRIPTION OF THE DRAWING FIGURES

Further features and advantages of the present invention will be evident from the following exemplary and non-limiting description of the invention by way of a pedicle screw system as an example of a bone screw system by way of figures. The figures are merely schematic and only serve for the comprehension of the invention, wherein.

DETAILED DESCRIPTION

Figure 1:
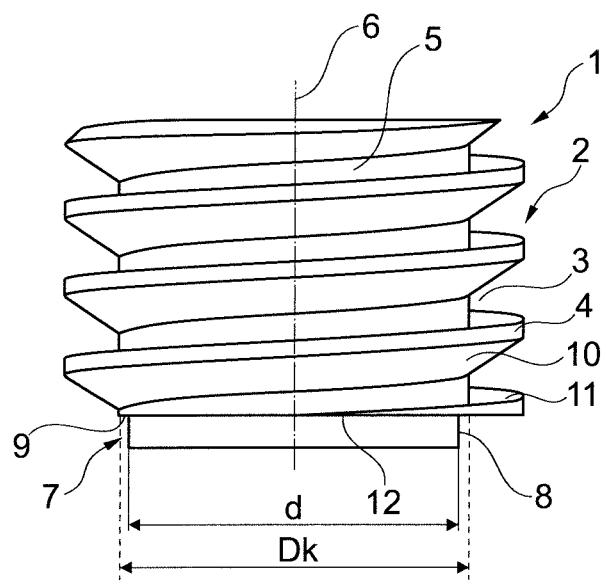
FIG. 1 shows a first clamping screw according to the state of the art in a front view.

FIG. 1 illustrates a clamping screw (set screw) 1 according to the state of the art in a lateral view. The clamping screw 1 is in the form of a set screw and includes a clamping screw thread 2 in the form of a male thread. It is a single-start thread and has a thread cut 3 and a thread elevation 4. The thread cut 3 and the thread elevation 4 extend spirally around a clamping screw base 5. FIG. 1 also illustrates a central longitudinal axis 6 of the clamping screw 1. On the run-in side of the clamping screw thread 2 the clamping screw is provided with a thread chamfer 7. The latter is in the faun of a step 8 and has a diameter d which is smaller than the thread core diameter $D_k$ of the clamping screw thread 2. Toward the clamping screw thread 2 the step 8 ends by a shoulder 9 which extends transversely to the longitudinal axis/screw axis 6 of the clamping screw 1. Due to this alignment of the shoulder 9, the thread 2 is chamfered orthogonally to the longitudinal axis 6 of the clamping screw 1. Thus, the first thread pitch is chamfered on the run-in side such that the radially outwardly extending thread profile (the thread elevation 4 delimited by thread flanks 10, 11) continuously increases in thickness in wedge shape in the circumferential direction starting with a crest 12, until the shoulder 9 does no longer intersect either of the thread flanks 10, 11 of the first thread pitch.

Figure 2:
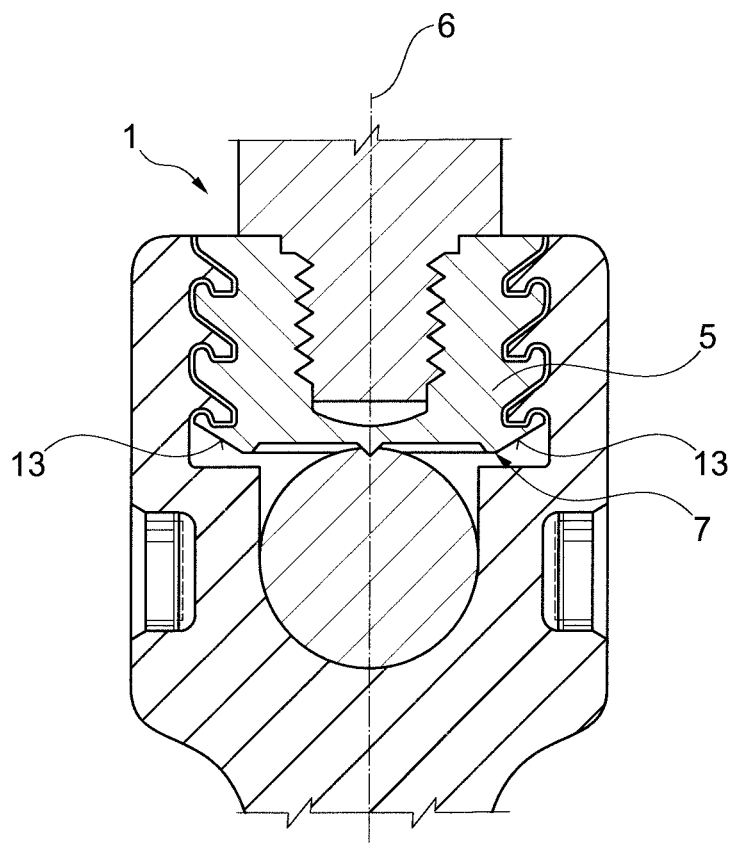
FIG. 2 shows a second clamping screw according to the state of the art in a front view.

FIG. 2 illustrates a different but similar known clamping screw 1 in which a thread chamfer 7 is not provided with a shoulder 9 extending orthogonally to the central longitudinal axis 6 but is provided with a circumferential beveling 13. In this case, too, the first thread pitch is chamfered on the run-in side so that the radially outwardly extending thread profile (the thread elevation 4 delimited by thread flanks 10, 11) continuously increases in thickness in wedge shape in the circumferential direction starting with a crest, until the circumferential beveling 13 does no longer intersect either of the thread flanks 10, 11 of the first thread pitch.

Figure 3:
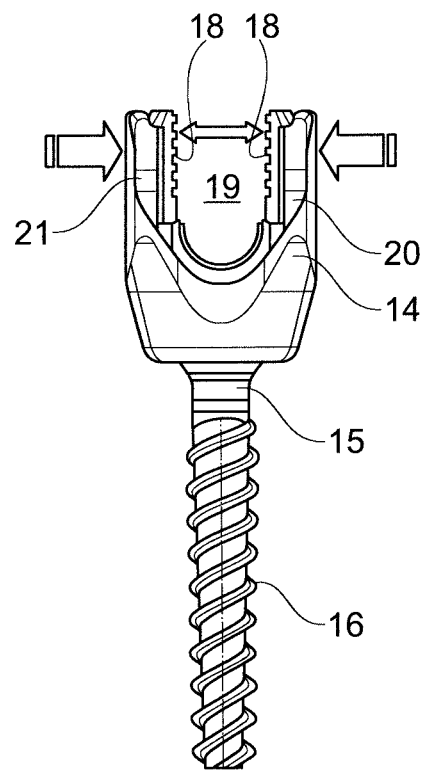
FIG. 3 shows a pedicle screw of a system according to the invention in a side view and marked deformations.
Figure 4:
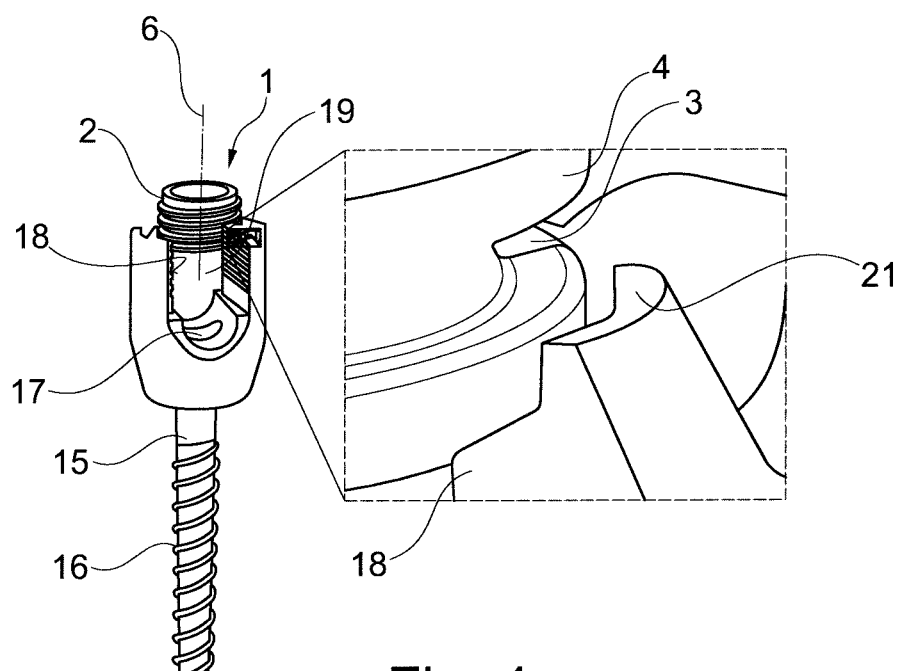
FIG. 4 shows the pedicle screw of FIG. 3 including the attached clamping screw.

FIGS. 3 and 4 illustrate the problem of deformation of a tulip 14 or receiving sleeve 14 of a pedicle screw 15. The latter is provided on the side opposite to the receiving sleeve 14 with a male thread 16, also referred to as bone thread 16, by which it may be screwed into a pedicle canal of a vertebra (as an example of a bone). On the side of the tulip 14, the pedicle screw 15 is provided with a screwing tool engagement 17 for this purpose. The tulip 14 is substantially U-shaped including a hole or slit 19 introduced in the axial direction and having a tulip thread 18. In other words, the tulip 14 can be formed by removing material from a hollow cylinder on radially opposing sides in the axial direction and the hole of the hollow cylinder is provided with the tulip thread 18. Two radially opposing sleeve wall portions or sleeve flanks 20, 21 whose inner surfaces facing each other delimit the hole 19 and are provided with the tulip thread 18 are retained of the hollow cylinder. The sleeve wall portions 20, 21 inter alia serve as tool contact surfaces for a handling tool (not shown) and, due to their slim shape, may deform in the radial direction especially by force applied by the tool. Deformations of this type are indicated in FIG. 3 and obstruct attachment and screwing-in of the clamping screw 1, as can be inferred from FIG. 4.

Figure 5:
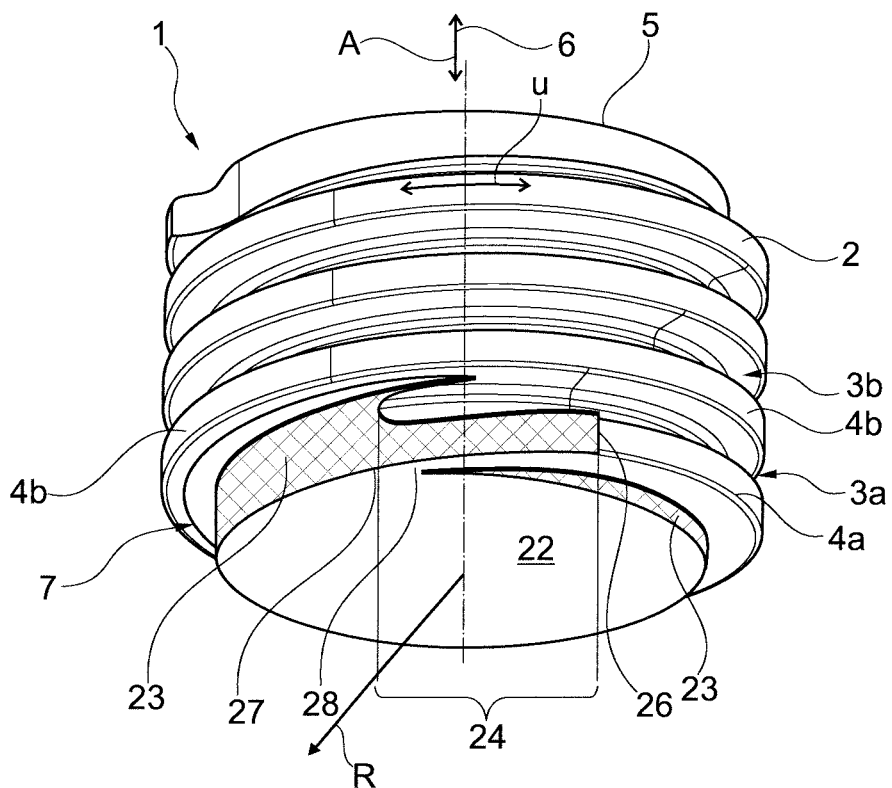
FIG. 5 shows a clamping screw according to the invention in a perspective view.

FIG. 5 illustrates the clamping screw 1 of a pedicle screw system or bone screw system according to the invention in a perspective view in which the lower end face 22 is visible. The clamping screw 1 is a stud screw and on the end face opposite to the end face 22 which is not evident in FIG. 5 includes a tool engagement for a screwing tool. The clamping screw 1 has a single-start clamping screw thread 2 in the form of a male thread. The thread elevation 4 thereof (including a first thread elevation 4a and a second thread elevation 4b) and the thread cut 3 thereof (including a first thread cut 3a and a second thread cut 3b) are marked in FIG. 5. The thread elevation 4 together with the thread cut 3 forms the thread pitch.

According to the invention, the clamping screw 1 is provided with a thread chamfer 7 on the run-in side. The circumferential surface 23 is marked by cross-hatching in the FIGS. 5, 7 and 8 and is formed in parallel to the central longitudinal axis 6 of the clamping screw 1. The thread chamfer 7 includes a transition section 24 as well as a subarea 25 at a constant radial distance from the central longitudinal axis 6. The radial distance of the circumferential surface 23 from the central longitudinal axis 6 on the run-out side of the transition section 24, viz. at the transition 26 from the transition section 24 to the not chamfered thread elevation 4, corresponds to the outer thread radius. The radial distance of the circumferential surface 23 from the central longitudinal axis 6 on the run-in side of the transition section 24, viz. at the transition 27 from the transition section 24 to the subarea 25 having a constant radius, is smaller than or equal to the thread core radius.

Figure 6:
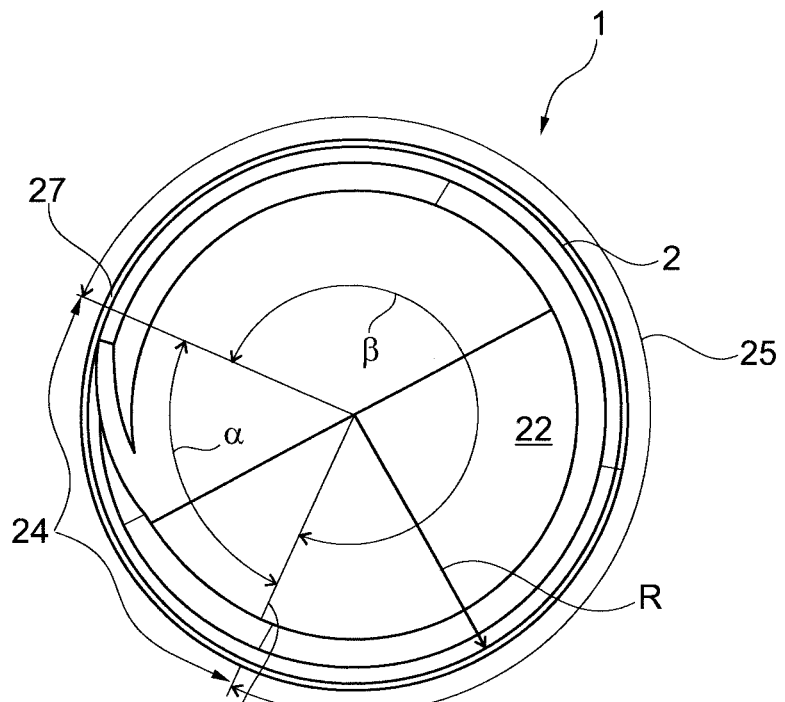
FIG. 6 shows the clamping screw of FIG. 5 in a bottom view.

In FIG. 6 the transition section 24 and the subarea 25 having a constant radius are separately marked. In the shown embodiment, the transition section 24 extends over an angular portion α of approx. 90°. The subarea 25 having a constant radius extends over an angular portion β of approx. 270°. FIG. 6 also shows the change of the distance of the circumferential surface in the radial direction R from the central longitudinal axis 6 on the run-in side. This is resulting in different distances of two points diametrically opposed vis-a-vis the central longitudinal axis 6 on the radial outer surface (cf. also FIG. 5) of the clamping screw 1 in the area of the end face 22. Hereinafter said distances will be referred to as diameter. A horizontal diameter, when viewed in FIG. 6, of the circumferential surface 23 at the end face 22 of the clamping screw 1, i.e. a distance between a point on the circumferential surface 23 in the transition area 24 and a point on the circumferential surface 23 in the subarea 25 having a constant radius, is larger than a vertical diameter, when viewed in FIG. 6, of the circumferential surface 23, i.e. a distance between two points on the circumferential surface 23 in the subarea 25 having a constant radius, at the end face 22 of the clamping screw 1. The clamping screw 1 can be inserted in a first position or inserting position in which the smaller diameter (the vertical diameter when viewed in FIG. 6) is provided between the two flanks of a deformed tulip 14. In other words, the circumferential surfaces 23 of the subarea 25 having a constant radius are adjacent to the flanks of the tulip 14. Subsequently, the clamping screw 1 is turned about 90 degrees into a second position or, resp., splayed position. Accordingly, the transition area 24 having the increasing radial distance of the circumferential surface 23 is screwed between the flanks of the tulip 14 and the flanks of the tulip 14 are splayed. The transition area 24 and, resp., the radial outer surface of the first thread elevation 4a are adjacent to the flank of the tulip 14.

Figure 7:
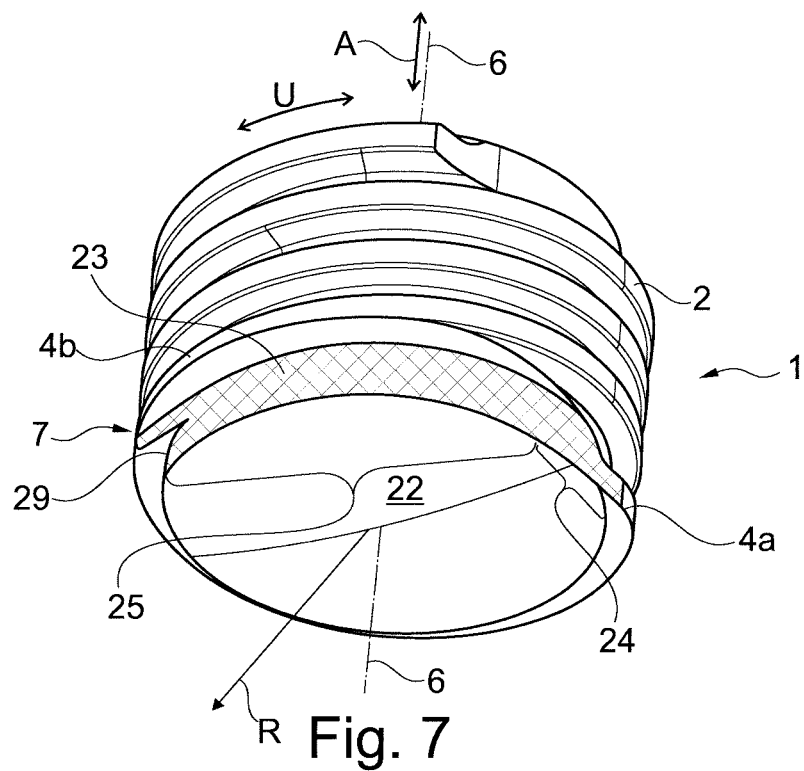
FIG. 7 shows a variant of the clamping screw of FIG. 5.
Figure 8:
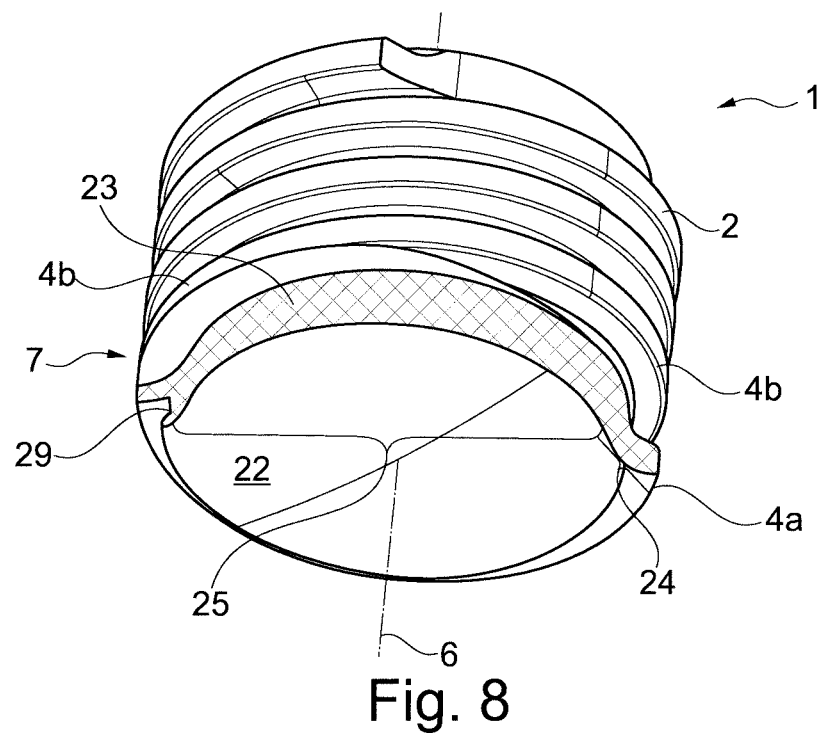
FIG. 8 shows another variant of the clamping screw of FIG. 5.

FIG. 7 shows a variant of the thread chamfer 7 according to the invention. In this one, too, the first thread elevation 4a is chamfered in the radial direction R, with the transition section 24 being formed to run out almost linearly or smoothly toward the not chamfered part of the first thread elevation 4a. Other than in the embodiment of FIGS. 5 and 6, the thread chamfer 7 does not follow the lead of the clamping screw thread 2 but is aligned transversely to the central longitudinal axis 6. For this reason, the second thread elevation 4b is chamfered not only in the radial direction R but also in the axial direction A. Hence a second transition section 29 is formed which is located on the side of the thread chamfer 7 opposite to the transition section 24 and is equal to the transition section 24. The embodiment of FIG. 8 is similar, but in this case the transition section 24 and the transition section 29 are curved. In the embodiments of FIGS. 7 and 8, the first thread elevation 4a especially critical when attaching and screwing in the clamping screw 1 is not weakened in the axial direction and is robust. Although the second thread elevation 4b is chamfered in the axial direction A, it is less critical in this respect, however, and the shown variants offer advantages in terms of manufacture when designing the thread chamfer 7.

Each of the FIGS. 5, 7 and 8 clearly illustrates that, according to the invention, the thread elevation 4 is not tapered and thus weakened by the thread chamfer 7 in the axial direction A. Rather, the first thread elevation 4a is chamfered in the radial direction R so that it is flattened 25 by the thread chamfer 7 in the radial direction R toward the central longitudinal axis 6 of the clamping screw 1. It is evident that the thread chamfer 7 merely chamfers the first thread elevation 4a in the radial direction R, wherein the second thread elevation 4b is not chamfered, however. None of the thread elevations 4a and 4b is chamfered in the axial direction A. When considered the other way round, the thread chamfer 7 starts at the transition section 24 with a large height in the axial direction A and is then formed to run out and becomes gradually thinner toward the end face 22. Hence it can be stated that the thread chamfer follows the lead of the clamping screw thread 2 or is formed to have the same lead. The smallest extension 28 of the thread chamfer 7 in the axial direction A is marked in FIG. 5 and is no more than 0.5 mm.

On the one hand, it is achieved by the thread chamfer 7 according to the invention that the locking screw 1 can be screwed in even when the tulip head 14 is deformed elastically inwardly by forces acting from outside. On the other hand, the thread chamfer 7 thus can be configured to be wide so that the risk of damage of the chamfer 7 and especially of the first thread elevation 4a during screwing is reduced.

The invention claimed is:

1. A clamping screw for a bone screw system which includes a bone screw comprising a tulip which forms a seat for a longitudinal support for surgical connection of adjacent bone screws and is provided with a tulip thread,
wherein the clamping screw comprises a longitudinal axis and a clamping screw thread for locking the longitudinal support by clamping in the seat,
wherein the clamping screw thread on a run-in side includes a radial thread cut at which the clamping screw thread is reduced or withdrawn in a radial direction, wherein the thread cut has a circumferential surface,
wherein the thread cut has a transition section in which the circumferential surface has a varying radial distance in the radial direction from the longitudinal axis of the clamping screw, and
wherein the radial distance between the circumferential surface and the longitudinal axis on a run-out side of the transition section corresponds to an outer thread radius, and the radial distance between the circumferential surface and the longitudinal axis on the run-in side of the transition section is smaller than a thread core radius.

2. The clamping screw according to claim 1, wherein the radial distance between the circumferential surface of the transition section and the longitudinal axis in a circumferential extension varies continuously and/or constantly.

3. The clamping screw according to claim 1, wherein the transition section in a circumferential direction extends over an angular portion a between approximately 20° and approximately 180°.

4. The clamping screw according to claim 1, wherein the thread cut is configured in a subarea in a pitch cylinder shape having a constant radial distance from the longitudinal axis.

5. The clamping screw according to claim 4, wherein the radial distance between the circumferential surface in the subarea having the constant radial distance is smaller than or equal to the thread core radius.

6. The clamping screw according to claim 4, wherein the subarea having a constant radial distance extends in the peripheral direction over an angular area β of at least 90°.

7. The clamping screw according to claim 1, wherein the thread cut ends where a thread crest of the clamping screw thread on the run-in side adopts its normal width.

8. The clamping screw according to claim 1, wherein the thread cut is configured to follow an elevation of the clamping screw thread.

9. A bone screw system comprising:
a bone screw having a tulip which forms a seat for a longitudinal support for surgical connection of adjacent bone screws and is provided with a tulip thread, and
a clamping screw according to claim 1 for screwing into the tulip thread and for locking the longitudinal support by clamping within the seat.

10. The clamping screw according to claim 1, wherein the clamping screw thread is of a one start design.

11. The clamping screw according to claim 1, wherein the circumferential surface is formed parallel to the central longitudinal axis of the clamping screw.

12. A clamping screw for a bone screw system which includes a bone screw comprising a tulip which forms a seat for a longitudinal support for surgical connection of adjacent bone screws and is provided with a tulip thread,
wherein the clamping screw comprises a longitudinal axis and a clamping screw thread for locking the longitudinal support by clamping in the seat,
wherein the clamping screw thread on a run-in side includes a radial thread cut at which the clamping screw thread is reduced or withdrawn in a radial direction, wherein the thread cut has a circumferential surface,
wherein the thread cut has a transition section in which the circumferential surface has a varying radial distance in the radial direction from the longitudinal axis of the clamping screw, wherein the radial distance between the circumferential surface and the longitudinal axis on a run-out side of the transition section corresponds to an outer thread radius, and the radial distance between the circumferential surface and the longitudinal axis on the run-in side of the transition section is smaller than a thread core radius, and wherein the radial distance between the circumferential surface of the transition section and the longitudinal axis in a circumferential extension varies continuously and/or constantly.

13. The clamping screw according to claim 12, wherein the transition section in a circumferential direction extends over an angular portion a between approximately 20° and approximately 180°.

14. The clamping screw according to claim 12, wherein the thread cut is configured in a subarea in a pitch cylinder shape having a constant radial distance from the longitudinal axis.

15. The clamping screw according to claim 14, wherein the radial distance between the circumferential surface in the subarea having the constant radial distance is smaller than or equal to the thread core radius.

16. The clamping screw according to claim 14, wherein the subarea having a constant radial distance extends in the peripheral direction over an angular area $\beta$ of at least 90°.

17. The clamping screw according to claim 12, wherein the thread cut ends where a thread crest of the clamping screw thread on the run-in side adopts its normal width.

18. The clamping screw according to claim 12, wherein the thread cut is configured to follow an elevation of the clamping screw thread.

19. The clamping screw according to claim 12, wherein the clamping screw thread is of a one start design.

20. A bone screw system comprising:
a bone screw having a tulip which forms a seat for a longitudinal support for surgical connection of adjacent bone screws and is provided with a tulip thread, and
a clamping screw according to claim 12 for screwing into the tulip thread and for locking the longitudinal support by clamping within the seat.

* * * * *